United States Patent [19]

Theobald et al.

[11] 4,385,924
[45] May 31, 1983

[54] 1,2-OXAZOLYL ALKYL CARBAMATES, AND THEIR USE AS HERBICIDES

[75] Inventors: Hans Theobald, Limburgerhof; Bruno Wuerzer, Otterstadt; Karl Kiehs, Lampertheim, all of Fed. Rep. of Germany

[73] Assignee: BASF Aktiengesellschaft, Fed. Rep. of Germany

[21] Appl. No.: 201,801

[22] Filed: Oct. 29, 1980

[30] Foreign Application Priority Data

Oct. 31, 1979 [DE] Fed. Rep. of Germany ....... 2943965

[51] Int. Cl.³ .................... A01N 43/80; C07D 261/14
[52] U.S. Cl. ......................................... 71/88; 548/247
[58] Field of Search ............................. 71/88; 548/247

[56] References Cited

U.S. PATENT DOCUMENTS

| | | | |
|---|---|---|---|
| 2,695,225 | 11/1954 | Witman . | |
| 3,116,995 | 1/1964 | Willard et al. . | |
| 3,652,575 | 3/1972 | Hutton et al. | 548/247 |
| 3,904,669 | 9/1975 | Boroschewski et al. | 71/88 |
| 4,067,726 | 1/1978 | Sasse et al. | 71/88 |
| 4,124,591 | 11/1978 | Eicken et al. | 548/247 |
| 4,227,915 | 10/1980 | D'Amico | 71/88 |
| 4,229,204 | 10/1980 | Howe | 548/247 |
| 4,256,480 | 3/1981 | Guigues et al. | 71/88 |

FOREIGN PATENT DOCUMENTS 54-55564  5/1979  Japan ...................... 71/88
574995  1/1946  United Kingdom .

Primary Examiner—Anton H. Sutto
Attorney, Agent, or Firm—Keil & Witherspoon

[57] ABSTRACT

1,2-Oxazolyl alkyl carbamates of the formula

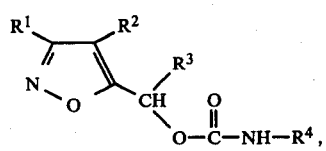

where $R^1$ denotes alkyl of a maximum of 6 carbon atoms, alkoxyalkyl of a maximum of 3 carbon atoms, or alkoxycarbonyl of a maximum of 5 carbon atoms, $R^2$ denotes hydrogen, or unsubstituted or halogen-substituted alkyl of a maximum of 3 carbon atoms, $R^3$ denotes hydrogen, or alkyl of a maximum of 3 carbon atoms, and $R^4$ denotes alkyl or cycloalkyl of a maximum of 6 carbon atoms, substituted or unsubstituted phenyl, or naphthyl, methylenedioxyphenyl, ethylenedioxyphenyl, benzofuranyl, dihydrobenzofuranyl or indanyl; the manufacture of such compounds, their use for combating unwanted plant growth, and herbicides containing these compounds.

7 Claims, No Drawings

1,2-OXAZOLYL ALKYL CARBAMATES, AND THEIR USE AS HERBICIDES

The present invention relates to 1,2-oxazolyl alkyl carbamates, a process for their manufacture, herbicides containing these compounds as active ingredients, and a process for combating unwanted plant growth with these compounds.

It is known that carbamates are suitable for combating unwanted plant growth. For instance, isopropyl N-phenylcarbamate combats grasses (German No. 833,274), the action being mainly via the roots. To bring the agent into contact with the roots, it is thus necessary for the soil to be adequately moist; consequently, the effectiveness of the herbicide depends on precipitation conditions.

Isopropyl N-3-chlorophenylcarbamate (U.S. Pat. No. 2,695,225) offers an improvement in herbicidal action on the preferred preemergence application. The use of methyl N-3,4-dichlorophenylcarbamate for combating unwanted plants on both pre- and postemergence application has also been disclosed (U.S. Pat. No. 3,116,995). The active ingredient is suitable for combating weeds in large-seed Leguminosae and rice, application being effected preemergence or soon after emergence when the plants are very small.

Furthermore, 1,2-oxazolylmethylthiol carbamates having a herbicidal action have been disclosed (German Laid-Open Application DE-OS No. 2,633,790). Compared with other prior art thiol carbamates, these compounds have a different and broader spectrum of action. Because their vapor pressure is low, they need not be incorporated into the soil before sowing.

We have now found that 1,2-oxazolyl alkyl carbamates of the formula

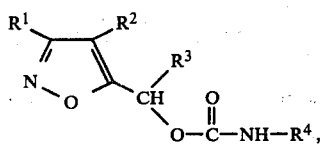

where $R^1$ is alkyl of a maximum of 6 carbon atoms, alkoxyalkyl of a maximum of 3 carbon atoms, or alkoxycarbonyl of a maximum of 5 carbon atoms, $R^2$ denotes hydrogen, or unsubstituted or halogen-substituted alkyl of a maximum of 3 carbon atoms, $R^3$ denotes hydrogen, or alkyl or a maximum of 3 carbon atoms, and $R^4$ denotes alkyl or cycloalkyl of a maximum of 6 carbon atoms, phenyl which is unsubstituted or substituted by halogen, nitro, cyano, or alkyl, alkoxy, haloalkyl, haloalkoxy, alkanoyl or alkoxycarbonyl of a maximum of 5 carbon atoms, or by cycloalkyl of a maximum of 6 carbon atoms, or $R^4$ denotes naphthyl, methylenedioxyphenyl, ethylenedioxyphenyl, benzofuranyl, dihydrobenzofuranyl or indanyl, have a herbicidal action on both pre- and postemergence application and are at the same time tolerated by crop plants. They have an action superior to that of prior art herbicidal (thiol) carbamates on broadleaved unwanted plants.

In formula I, $R^1$ denotes linear or branched alkyl of a maximum or 6, preferably a maximum of 4, carbon atoms, such as methyl, ethyl, n-propyl, isopropyl, n-butyl, isobutyl, sec-butyl, tert-butyl, n-pentyl, 1-methyl-n-butyl, n-hexyl, and 1-methyl-n-pentyl, linear or branched alkoxyalkyl of a maximum of 3 carbon atoms, such as methoxymethyl and methoxyethyl, or alkoxycarbonyl of a maximum of 5, especially a maximum of 4, carbon atoms, such as methoxycarbonyl, ethoxycarbonyl, n-propoxycarbonyl, isopropoxycarbonyl and the 4 isomeric butoxycarbonyl radicals; $R^2$ denotes, in addition to hydrogen, unsubstituted or halogen-substituted alkyl of a maximum of 3 carbon atoms, such as methyl, chloromethyl, ethyl, 2-chloroethyl, n-propyl and isopropyl; $R^3$ denotes, in addition to hydrogen, alkyl of a maximum of 3 carbon atoms, such as methyl, ethyl and propyl; and $R^4$ denotes linear or branched alkyl of a maximum of 6, especially a maximum of 4, carbon atoms, such as methyl, ethyl, isopropyl and the 4 isomeric butyl radicals, cycloalkyl of a maximum of 6 carbon atoms, such as cyclopropyl, cyclobutyl, cyclopentyl, and cyclohexyl, unsubstituted phenyl or phenyl which is mono- or polysubstituted by halogen, nitro, cyano, linear or branched alkyl, alkoxy, haloalkyl, haloalkoxy, alkanoyl or alkoxycarbonyl, each of a maximum of 5, especially of a maximum of 3, carbon atoms, or by cycloalkyl of from 3 to 6 carbon atoms, such as 3-chlorophenyl, 3,4-dichlorophenyl, 3-fluoro-4-chlorophenyl, 4-fluorophenyl, 3-chloro-4-fluorophenyl, 4-chlorophenyl, 4-bromophenyl, 2,5-difluorophenyl, 3-nitro-4-methylphenyl, 3-chloro-4-cyanophenyl, 3-chloro-4-methylphenyl, 3-methylphenyl, 2-isopropylphenyl, 4-isopropylphenyl, 4-tert-butylphenyl, 3,4-dimethylphenyl, 2-ethylphenyl, 2,6-diethylphenyl, 3-trifluoromethylphenyl, 3-trifluoromethyl-4-chlorophenyl, 2-methyl-3-chlorophenyl, 2-methoxy-4-chlorophenyl, 2,4-dimethoxy-5-chlorophenyl, 4-methoxy-3-chlorophenyl, 4-difluoromethoxyphenyl, 3-methoxy-4-methylphenyl, 4-cyclopropylphenyl, 4-cyclohexylphenyl, 4-acetylphenyl, 4-propionylphenyl, 4-methoxycarbonylphenyl, 4-ethoxycarbonylphenyl, and 3-ethoxycarbonylphenyl; $R^4$ may further denote naphthyl, indanyl, benzofuranyl, 1,2-methylenedioxyphenyl, 1,2-ethylenedioxyphenyl and 2,3-dihydrobenzofuranyl.

The 1,2-oxazolyl alkyl carbamates of the formula I are obtained by reaction of 5-hydroxymethyl-1,2-oxazoles of the formula

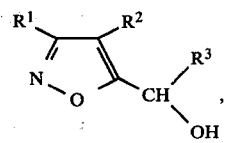

where $R^1$, $R^2$ and $R^3$ have the above meanings, with isocyanates of the formula $$OCN-R^4 \qquad III,$$

where $R^4$ has the above meanings, in the presence of absence of a diluent.

The reaction is carried out at a temperature of from $-50°$ to $+150°$ C., preferably from $+20°$ to $60°$ C. It may be advantageous to employ a diluent and a catalyst.

Suitable solvents are aromatic and aliphatic, optionally chlorinated, hydrocarbons, such as benzene, toluene, cresols, halobenzenes, methylene chloride, chloroform, and carbon tetrachloride, ethers, such as diethyl ether, tetrahydrofuran, and dioxane, ketones, such as diethyl ketone, methyl ethyl ketone, and diisopropyl ketone, and acetonitrile, dimethylformamide and dimethyl sulfoxide. Suitable catalysts are tertiary amines, such as triethylamine.

Some of the 5-hydroxymethyl-1,2-oxazoles of the formula II employed as starting materials are known; they may be prepared on the basis of prior art processes (Tetrahedron Letters, 4, 327–330, 1967). For instance the following 5-hydroxymethyl-1,2-oxazoles of the formula II are obtained in this manner:

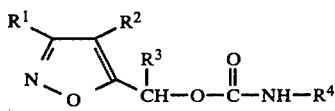

| $R^1$ | $R^2$ | $R^3$ | $n_D^{25}$/b.p. |
|---|---|---|---|
| $CH_3$ | H | H | 1.4773 |
| $CH_3$ | H | $CH_3$ | 1.4721 |
| $C_2H_5$ | H | H | 95–100° C./0.27 mbar |
| $C_2H_5$ | H | $CH_3$ | 92–93° C./0.13 mbar |
| $CH_3OCH_2$ | H | H | 1.4778 |
| $CH_3OCH_2$ | H | $CH_3$ | 118–121° C./1.1 mbar |
| $n\text{-}C_3H_7$ | H | H | 1.4738 |
| $n\text{-}C_3H_7$ | H | $CH_3$ | 1.4673 |
| $sec\text{-}C_4H_9$ | H | $CH_3$ | 1.4742 |
| $n\text{-}C_4H_9$ | H | $CH_3$ | 1.4692 |
| $C_2H_5OOC-$ | H | $CH_3$ | 1.4740 |
| $CH_3$ | $CH_2Cl$ | H | 1.4862 |
| $t\text{-}C_4H_9$ | H | H | 1.4725 |
| $t\text{-}C_4H_9$ | H | $CH_3$ | 1.4786 |
| $i\text{-}C_4H_9$ | H | $CH_3$ | 1.4735 |
| $i\text{-}C_4H_9$ | H | $CH_3$ | 119–125° C./0.67 mbar |
| $sec\text{-}C_4H_9$ | H | H | 1.4742 |

The isocyanates of the formula $OCN-R^4$ are known or may be readily prepared by known methods (Houben-Weyl, Methoden der organ. Chemie, 8, 119–128, Georg Thieme-Verlag, Stuttgart, 1952).

The 1,2-oxazolyl alkyl carbamates of the formula I according to the invention may be prepared analogously to the following example.

EXAMPLE 1

13.5 parts by weight of 3-isobutyl-5-(1'-hydroxyethyl)-1,2-oxazole is dissolved in 150 parts by volume of toluene; after the addition of 0.1 part by weight of triethylamine, 9.5 parts by weight of phenyl isocyanate is added dropwise. The mixture is then stirred for 1 hour at room temperature and for 4 hours at 50° C. After the mixture has cooled, the precipitate is filtered and washed with petroleum ether. There is obtained 14 parts by weight of 1-(3-isobutyl-1,2-oxazol-5-yl)-ethyl-N-phenyl carbamate as a crystalline substance; melting point: 105° C.

| $C_{16}H_{20}N_2O_3$ (288) | | |
|---|---|---|
| C | H | N |
| calc.: 66.7 | 7.0 | 9.7 |
| found: 66.7 | 6.5 | 10.3 |

For instance the following compounds of the formula

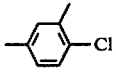

may be obtained analogously:

| No. | $R^1$ | $R^2$ | $R^3$ | $R^4$ | m.p. (°C.)/δ-values (MHz; LM) |
|---|---|---|---|---|---|
| 2 | $i\text{-}C_4H_9$ | H | $CH_3$ | 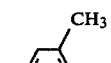 2,6-Cl,Cl-phenyl | 97–101 |
| 3 | $i\text{-}C_4H_9$ | H | $CH_3$ | 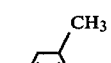 2-CH₃-phenyl | 106–109 |
| 4 | $CH_3OCH_2-$ | H | H | 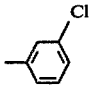 2-CH₃-phenyl | [80; D₆DMSO] 2.3 (3H); 4.5 (2H), 5.3 (2H), 6.1 (1H), 6.7–7.4 (4H) |
| 5 | $CH_3OCH_2-$ | H | H | 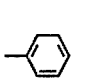 2-Cl-phenyl | 84–85 |
| 6 | $n\text{-}C_3H_7$ | H | $CH_3$ | 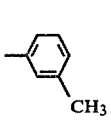 phenyl | 68–70 |
| 7 | $n\text{-}C_3H_7$ | H | $CH_3$ | 4-CH₃-phenyl | 60–63 |
| 8 | $n\text{-}C_3H_7$ | H | $CH_3$ | 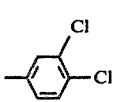 2,6-Cl,Cl-phenyl | 83–86 |

-continued
| No. | R¹ | R² | R³ | R⁴ | m.p. (°C.)/δ-values (MHz; LM) |
|---|---|---|---|---|---|
| 9 | sec-C₄H₉ | H | CH₃ |  | 74–76 |
| 10 | sec-C₄H₉ | H | CH₃ | 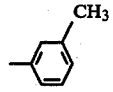 | 85–87 |
| 11 | sec-C₄H₉ | H | CH₃ | 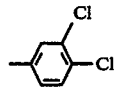 | 102–104 |
| 12 | CH₃OCH₂ | H | CH₃ | 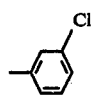 | [100; D₆DMSO] 1.7 (3H), 3.3 (3H), 4.45 (2H), 6.0 (1H), 6.5 (1H), 6.9–7.6 (4H) |
| 13 | CH₃OCH₂— | H | CH₃ | 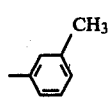 | [100; D₆DMSO] 1.45 (3H), 2.3 (3H), 3.3 (3H), 4.42 (2H), 5.96 (1H), 6.5 (1H), 6.7–7.3 (4H) |
| 14 | n-C₄H₉ | H | CH₃ |  | [100; D₆DMSO] 6.9 (3H), 1.1–1.7 (4H), 1.6 (3H), 2.6 (3H), 5.94 (1H), 6.4 (1H), 6.8–7.5 (5H), 9.8 (1H) |
| 15 | n-C₄H₉ | H | CH₃ | 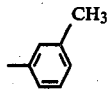 | [220; D₆DMSO] 0.9 (3H), 1.3 (2H), 1.45–1.7 (2 + 3H), 4.25 (3H), 2.55 (2H), 5.95 (1H), 6.4 (1H), 6.8 (1H), 7.1–7.3 (3H), 4.8 (1H) |
| 16 | n-C₄H₉ | H | CH₃ | 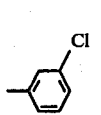 | [220; D₆DMSO] 0.9 (3H), 1.35 (2H), 1.5–1.7 (2H + 3H), 2.6 (2H), 5.96 (1H), 6.45 (1H), 7.05 (1H), 7.25–7.7 (3H), 10.2 (1H) |
| 17 | n-C₄H₉ | H | CH₃ | 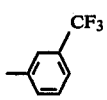 | [220; D₆DMSO] 0.9 (3H), 1.35 (2H), 1.5–1.7 (3H + 2H), 2.6 (2H), 6.05 (1H), 6.5 (1H), 7.3–8.0 (4H), 10.3 (1H) |
| 18 | H₅C₂OOC— | H | CH₃ |  | 59–61 |
| 19 | H₅C₂OOC— | H | CH₃ | 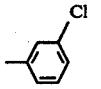 | 103–104 |
| 20 | H₅C₂OOC— | H | CH₃ | 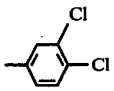 | 143–144 |
| 21 | H₅C₂OOC— | H | CH₃ | 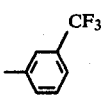 | 104–106 |

-continued

| No. | R¹ | R² | R³ | R⁴ | m.p. (°C.)/δ-values (MHz; LM) |
|---|---|---|---|---|---|
| 22 | CH₃ | H | CH₃ | 2,3-dihydrobenzofuran-5-yl | 109 |
| 23 | C₂H₅ | H | CH₃ | 2,3-dihydrobenzofuran-5-yl | 107–110 |
| 24 | t-C₄H₉ | H | CH₃ | 4-F-C₆H₄ | 112–114 |
| 25 | t-C₄H₉ | H | CH₃ | 3-CF₃-C₆H₄ | 86–87 |
| 26 | t-C₄H₉ | H | CH₃ | C₆H₅ | 86–87 |
| 27 | t-C₄H₉ | H | CH₃ | 3,4-Cl₂-C₆H₃ | [100; D₆DMSO] 1.3 (9H), 1.65 (3H), 5.98 (1H), 5.6 (1H), 7.3–7.8 (3H) |
| 28 | t-C₄H₉ | H | CH₃ | 4-Cl-3-CH₃? (4-Cl-phenyl) | 102–105 |
| 29 | t-C₄H₉ | H | CH₃ | C₆H₁₁ | 88–92 |
| 30 | CH₃ | H | CH₃ | 4-C₆H₁₁-C₆H₄ | 120–123 |
| 31 | CH₃ | H | CH₃ | 3-Cl-4-F-C₆H₃ | [60; D₆DMSO] 1.63 (3H), 2.25 (3H), 5.95 (1H), 6.4 (1H), 7.2–7.8 (3H) |
| 32 | t-C₄H₉ | H | CH₃ | 3-Cl-4-F-C₆H₃ | 122–123 |
| 33 | CH₃OCH₂— | H | CH₃ | C₆H₅ | [60; D₆DMSO] 1.6 (3H), 3.3 (3H), 4.4 (2H), 5.9 (1H), 6.2 (1H), 6.9–7 (5H), 7.7 (1H) |
| 34 | CH₃OCH₂— | H | CH₃ | 3,4-Cl₂-C₆H₃ | [270; CDCl₃ + D₆DMSO] 1.74 (3H), 3.25 (3H), 4.45 (2H), 6.05 (1H), 6.32 (1H), 7.18 (2H), 7.75 (1H), 8.44 (1H) |
| 35 | CH₃OCH₂— | H | CH₃ | 4-F-C₆H₄ | [60; D₆DMSO] 1.5 (3H), 3.15 (3H), 4.35 (2H), 5.9 (1H), 6.45 (1H), 6.8–7.5 (4H), 9.8 (1H) |
| 36 | CH₃OCH₂— | H | CH₃ | 3-CF₃-C₆H₄ | [60; D₆DMSO] 1.65 (3H), 3.2 (3H), 4.36 (2H), 5.9 (1H), 6.47 (1H), 7.2–7.85 (4H) |
| 37 | CH₃ | H | CH₃ | i-C₃H₇ | [60; CDCl₃] 1.16 (6H), 1.6 (3H), |

-continued
| No. | R¹ | R² | R³ | R⁴ | m.p. (°C.)/δ-values (MHz; LM) |
|---|---|---|---|---|---|
| | | | | | 2.25 (3H), 3.8 (1H), 5.3 (1H), 5.9 (1H), 6.1 (1H) |
| 38 | CH₃ | H | CH₃ | CH₃ | [60; CDCl₃] 1.55 (3H), 2.25 (3H), 2.75 (3H), 5.7 (1H), 5.85 (1H), 6.05 (1H) |
| 39 | C₂H₅ | H | CH₃ | 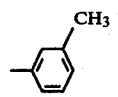 | 78 |
| 40 | C₂H₅ | H | CH₃ | 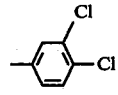 | 83 |
| 41 | C₂H₅ | H | CH₃ | 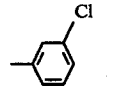 | 54 |
| 42 | C₂H₅ | H | CH₃ | 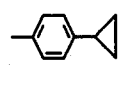 | 72 |
| 43 | C₂H₅ | H | CH₃ | 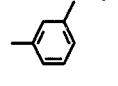 | 74–75 |
| 44 | C₂H₅ | H | CH₃ | 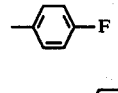 | 67 |
| 45 | C₂H₅ | H | CH₃ | 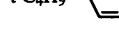 | 73–76 |
| 46 | CH₃ | H | CH₃ | 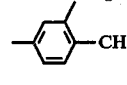 | 99–100 |
| 47 | CH₃ | H | CH₃ | 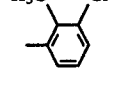 | 107–108 |
| 48 | CH₃ | H | CH₃ | 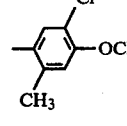 | 91–93 |
| 49 | CH₃ | H | CH₃ | 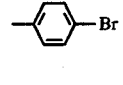 | 83–84 |
| 50 | CH₃ | H | CH₃ | 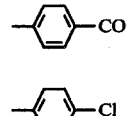 | 123 |
| 51 | CH₃ | H | CH₃ | 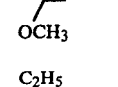 | 52–56 |
| 52 | CH₃ | H | CH₃ | 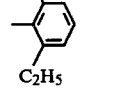 | 110–113 |

-continued
| No. | R¹ | R² | R³ | R⁴ | m.p. (°C.)/δ-values (MHz; LM) |
|---|---|---|---|---|---|
| 53 | CH₃ | H | CH₃ | 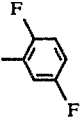 | 62 |
| 54 | CH₃ | H | CH₃ |  | 95–98 |
| 55 | CH₃ | H | CH₃ | C₅H₉ | 40–42 |
| 56 | CH₃ | H | CH₃ |  | 62–67 |
| 57 | CH₃ | H | CH₃ |  | 79–82 |
| 58 | i-C₃H₇ | H | CH₃ |  | 113–114 |
| 59 | CH₃ | H | CH₃ |  | 98–100 |
| 60 | CH₃ | H | CH₃ |  | 56–60 |
| 61 | C₂H₅ | H | CH₃ |  | 87–88 |
| 62 | t-C₄H₉ | CH₂Cl | H |  | [60; CDCl₃] 1.35 (9H), 3.95 (2H), 4.64 (2H), 6.6–7.4 (5H) |
| 63 | t-C₄H₉ | CH₂Cl | H |  | [100; D₆DMSO] 1.45 (9H), 2.3 (3H), 4.53 (2H), 4.9 (2H), 7.3 (2H), 7.42 (1H) |
| 64 | t-C₄H₉ | H | H |  | 92–96 |
| 65 | t-C₄H₉ | CH₂Cl | H |  | [60; D₆DMSO] 1.4 (9H), 4.5 (2H), 4.83 (2H), 6.4–7.6 (4H) |
| 66 | CH₃ | H | H |  | [60; D₆DMSO] 2.1–2.2 (6H), 5.2 (2H), 6.32 (1H), 6.7–7.3 (4H) |
| 67 | CH₃ | H | H |  | [100; D₆DMSO] 2.24 (3H), 5.32 (2H), 6.5 (1H), 7.3–8.0 (4H) |
| 68 | CH₃ | CH₂Cl | H |  | [60; CDCl₃] 2.11 (3H), 2.24 (3H), 4.1 (2H), 4.78 (2H), 6.8–7.4 (5H) |

-continued

| No. | R¹ | R² | R³ | R⁴ | m.p. (°C.)/δ-values (MHz; LM) |
|---|---|---|---|---|---|
| 69 | CH₃ | H | H |  4-Cl-C₆H₄-CH₂- | [100; D₆DMSO] 2.28 (3H), 5.3 (2H), 6.5 (1H), 7.0–7.7 (4H) |
| 70 | CH₃ | H | H |  C₆H₅-CH₂- | [60; D₆DMSO] 2.23 (3H), 5.3 (2H), 6.4 (1H), 6.9–7.6 (5H), 9.82 (1H) |
| 71 | C₂H₅ | H | H |  2,3-Cl₂-C₆H₃-CH₂- | 100–102 |
| 72 | t-C₄H₉ | H | H |  2,3-Cl₂-C₆H₃-CH₂- | 157–158 |
| 73 | C₂H₅ | H | H |  C₆H₅-CH₂- | [60; CDCl₃] 1.2 (3H), 2.6 (2H), 5.2 (2H), 6.14 (1H), 6.9–7.5 (5H), 7.95 (1H) |
| 74 | C₂H₅ | H | H |  3-CF₃-C₆H₄-CH₂- | [60; CDCl₃] 1.27 (3H), 2.7 (2H), 5.25 (2H), 6.22 (1H), 7.1–7.4 (4H), 8.2 (1H) |
| 75 | C₂H₅ | H | H |  3-Cl-C₆H₄-CH₂- | [60; D₆DMSO] 1.3 (3H), 2.72 (2H), 5.38 (2H), 6.5 (1H), 6.9–7.2 (4H), 10.05 (1H) |
| 76 | CH₃ | CH₂Cl | H |  2,3-Cl₂-C₆H₃-CH₂- | [60; D₆DMSO] 2.1 (3H), 4.4 (2H), 4.8 (2H), 7.3 (2H), 7.6 (1H), 10.1 (1H) |
| 77 | C₂H₅ | CH₂Cl | H |  3-Cl-C₆H₄-CH₂- | [60; DCDl₃] 1.2 (3H), 2.5 (2H), 4.1 (2H), 4.8 (2H), 6.9–7.7 (6H), 8.1 (1H) |
| 78 | C₂H₅ | CH₂Cl | H |  3-CF₃-C₆H₄-CH₂- | [60; CDCl₃] 1.18 (3H), 2.5 (2H), 4.0 (2H), 4.7 (2H), 6.0–7.7 (4H) |
| 79 | CH₃ | CH₂Cl | H |  3-CF₃-C₆H₄-CH₂- | [60; CDCl₃] 2.2 (3H), 4.1 (2H), 4.75 (2H), 7.1–7.8 (4H) |
| 80 | CH₃ | H | CH₃ |  3-CF₃-C₆H₄-CH₂- | [60; CDCl₃] 1.6 (3H), 2.2 (3H), 5.9 (1H), 6.04 (1H), 7.2–7.9 (5H) |
| 81 | CH₃ | H | CH₃ |  4-F-C₆H₄-CH₂- | [60; CDCl₃] 1.5 (3H), 2.2 (3H), 5.87 (1H), 5.92 (1H), 6.7–7.4 (5H) |
| 82 | CH₃ | H | CH₃ |  C₆H₅-CH₂- | [60; CDCl₃] 1.52 (3H), 1.68 (3H), 5.9 (1H), 5.97 (1H), 6.9–7.5 (6H) |
| 83 | t-C₄H₉ | H | H | 3-CF₃-C₆H₄-CH₂- | 84 |

-continued

| No. | R¹ | R² | R³ | R⁴ | m.p. (°C.)/δ-values (MHz; LM) |
|---|---|---|---|---|---|
| 84 | t-C₄H₉ | H | H | 4-F-phenyl | 140–141 |
| 85 | t-C₄H₉ | H | H | 3-CH₃-phenyl | 80–83 |
| 86 | CH₃ | H | CH₃ | 3,4-(OCH₂CH₂O)-phenyl (benzodioxane) | 101–105 |
| 87 | CH₃ | H | CH₃ | 3-Cl-4-OCH₃-phenyl | 92–93 |
| 88 | CH₃ | H | CH₃ | 2-i-C₃H₇-phenyl | 72–75 |
| 89 | C₂H₅ | H | CH₃ | C₆H₁₁ | 73 |
| 90 | CH₃ | H | CH₃ | 3-Cl-4-CH₃-phenyl | [60; CDCl₃] 1.45 (3H), 2.1 (6H), 5.7–6.0 (2H), 6.95 (2H), 7.2–7.4 (2H) |
| 91 | CH₃ | H | CH₃ | 3-F-phenyl | [60; CDCl₃] 1.52 (3H), 2.15 (3H), 5.7–6.1 (2H), 6.5–7.4 (4H), 7.76 (1H) |
| 92 | CH₃ | H | CH₃ | 4-Cl-phenyl | [60; CDCl₃] 1.5 (3H), 2.3 (3H), 5.9–6.2 (2H), 7.2–7.5 (4H) |
| 93 | CH₃ | H | CH₃ | 2-C₂H₅-phenyl | [60; CDCl₃] 1.3 (3H), 1.65 (3H), 2.3 (3H), 2.6 (2H), 5.9–6.2 (2H), 6.7 (1H), 7.1–7.9 (4H) |
| 94 | CH₃ | H | CH₃ | C₆H₁₁ | [60; CDCl₃] 0.9–1.9 (10H), 1.45 (3H), 2.05 (3H), 3.3 (1H), 4.9 (1H), 5.1–6.0 (2H) |
| 95 | CH₃ | H | CH₃ | 4-OCHF₂-phenyl | [60; CDCl₃] 1.5 (3H), 2.15 (2H), 5.7–6.0 (2H), 6.35 (1H), 6.8–7.5 (5H) |
| 96 | CH₃ | H | CH₃ | 2,3-(CH₃)₂-phenyl | [60; CDCl₃] 1.5 (3H), 2.0 (3H), 2.1 (6H), 5.7–6.0 (2H), 6.35 (1H), 6.7–7.5 (3H) |
| 97 | CH₃ | H | CH₃ | indanyl | [60; CDCl₃] 1.76 (3H), 2.2 (2H), 2.4 (3H), 3.0 (4H), 5.9–6.3 (2H), 7.1–7.5 (4H) |
| 98 | CH₃ | H | CH₃ | 3-CH₃-phenyl | [60; D₆DMSO] 1.55 (3H), 2.16 (6H), 5.85 (1H), 6.2 (1H), 6.6–7.3 (4H), 9.6 (1H) |

-continued

| No. | R¹ | R² | R³ | R⁴ | m.p. (°C.)/δ-values (MHz; LM) |
|---|---|---|---|---|---|
| 99 | CH₃ | H | CH₃ | 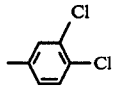 | [60; D₆DMSO] 1.63 (3H), 2.2 (3H), 5.95 (1H), 6.3 (1H), 7.2–7.8 (3H), 10.1 (1H) |
| 100 | CH₃ | H | CH₃ | 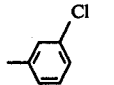 | [60; D₆DMSO] 1.6 (3H), 2.2 (3H), 5.92 (1H), 6.3 (1H), 6.8–7.6 (4H), 10.05 (1H) |
| 101 | CH₃ | H | CH₃ | 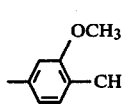 | [60; CDCl₃] 1.6 (3H), 2.1 (3H), 2.2 (3H), 3.7 (3H), 5.8–6.1 (2H), 6.75–7.2 (3H), 7.7 (1H) |
| 102 | CH₃ | H | CH₃ | 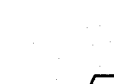 | [60; CDCl₃] ? (9H), 1.4 (3H), 2.2 (3H), 5.8–6.1 (2H), 7.1–7.3 (5H) |
| 103 | C₂H₅ | H | CH₃ | 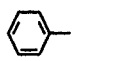 | [60; CDCl₃] 1.2 (3H), 1.6 (3H), 2.65 (2H), 5.7–6.2 (2H), 6.9–7.5 (6H) |
| 104 | CH₃ | H | CH₃ | 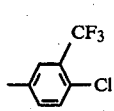 | [60; CDCl₃] 1.6 (3H), 2.2 (3H), 5.7–6.2 (2H), 7.2–7.8 (3H), 7.96 (1H) |
| 105 | CH₃ | CH₂Cl | H | 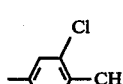 | [60; CDCl₃] 2.1 (6H), 4.1 (2H), 4.7 (2H), 7.1–7.6 (4H) |
| 106 | i-C₄H₉ | H | CH₃ | 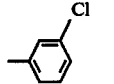 | 58–62 |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, ddimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound 1 is mixed with 10 parts by weight of N-methyl-α-pyrrolidone. A mixture is obtained which is suitable for application in the form of very fine drops.

II. 20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound 37 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound 5 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 20 is intimately mixed with 97 parts by weight of particulate kaolin. A dust is obtained containing 3% by weight of the active ingredient.

VII. 30 parts by weight of compound 96 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound 11 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents containing them may be applied pre- or postemergence, either to the location before the unwanted plants have germinated from seed or sprouted from vegetative plant parts, or to the leaves of the unwanted and crop plants. A special application technique is to spray the active ingredients with the aid of spraying equipment in such a way that the leaves of sensitive crop plants are if possible not hit; the active ingredients reach the soil or unwanted plants growing below the crop plants (post-directed, lay-by treatment). Application rates depend on the time of the year and the growth stage, and vary from 0.1 to 15 kg/ha and more, the higher rates being particularly suitable for the total elimination of vegetation.

The influence of various representatives of the 1,2-oxazolyl alkyl carbamates according to the invention on the growth of unwanted and crop plants is demonstrated in the following greenhouse experiments.

The vessels employed were plastic flowerpots having a volume of 300 cm$^3$ and which were filled with a sandy loam containing about 1.5% humus. The seeds of the test plants (cf. Table 1) were sown shallow, and separately, according to species. For the preemergence treatment, the active ingredients were applied to the surface of the soil immediately after the seeds has been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. No cover was placed on the vessels.

The pots were set up in the greenhouse-species from warmer areas at from 25° to 40° C., and species from moderate climates at 15° to 30° C. The experiments were run for from 3 to 6 weeks. During this period, the plants were tended and their reactions to the various treatments assessed. Tables 2 to 12 contain the compounds investigated and the application rates in kg/ha of active ingredient. The plants used for the tests are given in Table 1. The scale used for assessment was 0 to 100, 0 denoting no damage or normal emergence, and 100 denoting nonemergence or complete destruction of at least the visible plant parts.

TABLE 1

| List of plant names | | |
|---|---|---|
| Botanical name | Abbreviation in tables | Common name |
| *Allium cepa* | — | onion |
| *Alopecurus myosuroides* | *Alopec. myos.* | slender foxtail |
| *Arachys hypogaea* | *Arachys hyp.* | groundnuts |
| *Avena fatua* | — | wild oats |
| *Beta vulgaris* | — | sugarbeets |
| *Brassica napus* | — | rape |
| *Bromus spp.* | — | brome |

TABLE 1-continued

List of plant names

| Botanical name | Abbreviation in tables | Common name |
|---|---|---|
| Cassia spp. | — | |
| Centaurea cyanus | Cent. cyan. | cornflower |
| Chenopodium album | Chenopod. alb. | lambsquarters |
| Datura stramonium | — | jimsonweed |
| Daucus carota | — | carrots |
| Desmodium tortuosum | | |
| Glycine max | — | soybeans |
| Lolium multiflorum | | Italian ryegrass |
| Matricaria spp. | Matric. spp. | chamomile |
| Nicandra physaloides | Nicand. phys. | apple-of-Peru |
| Sesbania exaltata | Sesbania exalt. | hemp sesbania |
| Sinapis alba | — | white mustard |
| Sorghum bicolor | Sorgh. bicol. | wild cane |
| Solanum nigrum | Solan. nigr. | black nightshade |
| Stellaria media | — | chickweed |
| Triticum aestivum | Tritic. aest. | wheat |
| Mercurialis annua | Mercur. ann. | annual mercury |
| Oryza sativa | Oryza sat. | rice |

TABLE 2

Herbicidal action on *Lolium multiflorum*; preemergence application in the greenhouse $$\begin{array}{c} R^1 \\ \diagdown \\ N \diagup \\ \diagdown O \diagup \end{array} \overset{R^2}{\underset{CH}{\diagup}} \overset{R^3}{\underset{O-C-NH-R^4}{\diagdown}} \overset{}{\underset{\parallel}{O}}$$

| Active ingredient no. | $R^1$ | $R^2$ | $R^3$ | $R^4$ | % damage at a rate of 3.0 kg a.i./ha |
|---|---|---|---|---|---|
| 98 | $CH_3$ | H | $CH_3$ | 3-methylphenyl | 100 |
| 82 | $CH_3$ | H | $CH_3$ | phenyl | 100 |
| 81 | $CH_3$ | H | $CH_3$ | 4-fluorophenyl | 100 |
| 91 | $CH_3$ | H | $CH_3$ | 3-fluorophenyl | 100 |
| 103 | $C_2H_5$ | H | $CH_3$ | phenyl | 100 |
| 39 | $C_2H_5$ | H | $CH_3$ | 3-methylphenyl | 100 |
| 41 | $C_2H_5$ | H | $CH_3$ | 3-chlorophenyl | 100 |
| 44 | $C_2H_5$ | H | $CH_3$ | 4-fluorophenyl | 100 |
| 53 | $CH_3$ | H | $CH_3$ | 3,5-difluorophenyl | 100 |
| 58 | $i$-$C_3H_7$ | H | $CH_3$ | 3-methylphenyl | 100 |
| 31 | $CH_3$ | H | $CH_3$ | 3-chloro-4-fluorophenyl | 100 |
| 33 | $CH_3OCH_2$ | H | $CH_3$ | phenyl | 100 |
| 35 | $CH_3OCH_2$ | H | $CH_3$ | 4-fluorophenyl | 100 |
| 68 | $CH_3$ | $CH_2Cl$ | H | 3-methylphenyl | 100 |
| 70 | $CH_3$ | H | H | phenyl | 100 |
| 77 | $C_2H_5$ | $CH_2Cl$ | H | 3-chlorophenyl | 100 |
| 62 | tert.-$C_4H_9$ | $CH_2Cl$ | H | 4-fluorophenyl | 100 |
| 65 | tert.-$C_4H_9$ | $CH_2Cl$ | H | 3-chlorophenyl | 100 |
| 5 | $CH_3$—O—$CH_2$ | H | H | 3-chlorophenyl | 95 |
| 6 | n-$C_3H_7$ | H | $CH_3$ | phenyl | 95 |
| 9 | sec-$C_4H_9$ | H | $CH_3$ | phenyl | 100 |

TABLE 2-continued
Herbicidal action on *Lolium multiflorum*; preemergence application in the greenhouse $$\begin{array}{c} R^1 \quad R^2 \\ \diagdown \quad \diagup \\ \| \quad \| \quad R^3 \\ N \quad C \!-\! CH \\ \diagdown O \diagup \quad | \\ \quad \quad O\!-\!\overset{O}{\underset{\|}{C}}\!-\!NH\!-\!R^4 \end{array}$$

| Active ingredient no. | $R^1$ | $R^2$ | $R^3$ | $R^4$ | % damage at a rate of 3.0 kg a.i./ha |
|---|---|---|---|---|---|
| 1 | i-$C_4H_9$ | H | $CH_3$ | –phenyl | 100 |
| 7 | n-$C_3H_7$ | H | $CH_3$ | –(3-$CH_3$)phenyl | 90 |
| 13 | $CH_3OCH_2$ | H | $CH_3$ | –(3-$CH_3$)phenyl | 100 |
| 14 | n-$C_4H_9$ | H | $CH_3$ | –phenyl | 100 |
| 15 | n-$C_4H_9$ | H | $CH_3$ | –(3-$CH_3$)phenyl | 100 |
| 16 | n-$C_4H_9$ | H | $CH_3$ | –(3-Cl)phenyl | 100 |

TABLE 4
Postemergence action on *Lolium multiflorum* in the greenhouse $$\begin{array}{c} R^1 \quad R^2 \\ \diagdown \quad \diagup \\ \| \quad \| \quad R^3 \\ N \quad C \!-\! CH \\ \diagdown O \diagup \quad | \\ \quad \quad O\!-\!\overset{O}{\underset{\|}{C}}\!-\!NH\!-\!R^4 \end{array}$$

| Active ingredient no. | $R^1$ | $R^2$ | $R^3$ | $R^4$ | % damage at a rate of 3.0 kg a.i./ha |
|---|---|---|---|---|---|
| 100 | $CH_3$ | H | $CH_3$ | –(3-Cl)phenyl | 100 |
| 98 | $CH_3$ | H | $CH_3$ | –(3-$CH_3$)phenyl | 100 |
| 82 | $CH_3$ | H | $CH_3$ | –phenyl | 100 |
| 103 | $C_2H_5$ | H | $CH_3$ | –phenyl | 100 |
| 39 | $C_2H_5$ | H | $CH_3$ | –(3-$CH_3$)phenyl | 100 |
| 40 | $C_2H_5$ | H | $CH_3$ | –(3,4-$Cl_2$)phenyl | 100 |
| 41 | $C_2H_5$ | H | $CH_3$ | –(3-Cl)phenyl | 100 |

TABLE 3
Selective control of *Alopecurus myosuroides* in sugarbeets; preemergence application in the greenhouse

| Active ingredient no. | Formula | Appl. rate kg a.i./ha | Test plants and % damage | |
|---|---|---|---|---|
| | | | *Beta vulgaris* | *Alopecurus myosuroides* |
| 98 | $CH_3\!-\!\underset{N\diagdown O}{C}\!=\!\underset{CH_3}{C}\!-\!CH\!-\!O\!-\!\overset{O}{\underset{\|}{C}}\!-\!\underset{H}{N}\!-\!(3\text{-}CH_3)\text{phenyl}$ | 1.0 | 0 | 100 |
| | phenyl-$\underset{H}{N}\!-\!\overset{O}{\underset{\|}{C}}\!-\!O\!-\!CH(CH_3)_2$ (German 833,274) | 1.0 | 0 | 70 |
| | (3-Cl)phenyl-$\underset{H}{N}\!-\!\overset{O}{\underset{\|}{C}}\!-\!O\!-\!CH(CH_3)_2$ (U.S. Pat. No. 2,695,225) | 1.0 | 40 | 100 |

TABLE 4-continued

Postemergence action on *Lolium multiflorum* in the greenhouse

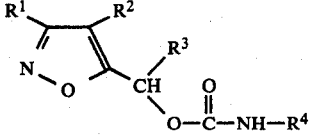

| Active ingredient no. | R¹ | R² | R³ | R⁴ | % damage at a rate of 3.0 kg a.i./ha |
|---|---|---|---|---|---|
| 44 | C₂H₅ | H | CH₃ |  | 100 |
| 53 | CH₃ | H | CH₃ | 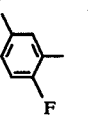 | 100 |
| 31 | CH₃ | H | CH₃ | 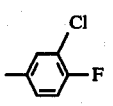 | 100 |
| 36 | CH₃OCH₂ | H | CH₃ | 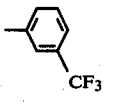 | 100 |
| 68 | CH₃ | CH₂Cl | H | 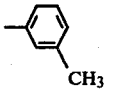 | 100 |
| 77 | C₂H₅ | CH₂Cl | H | 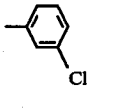 | 100 |
| 62 | tert-C₄H₉ | CH₂Cl | H |  | 100 |

TABLE 5

Postemergence action on *Sinapis alba* in the greenhouse

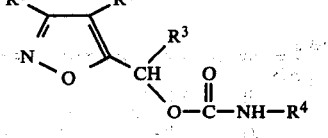

| Active ingredient no. | R¹ | R² | R³ | R⁴ | % damage at a rate of 3.0 kg a.i./ha |
|---|---|---|---|---|---|
| 86 | CH₃ | H | CH₃ |  | 100 |
| 90 | CH₃ | H | CH₃ |  | 100 |
| 82 | CH₃ | H | CH₃ |  | 100 |
| 81 | CH₃ | H | CH₃ | 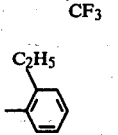 | 100 |
| 80 | CH₃ | H | CH₃ |  | 100 |
| 93 | CH₃ | H | CH₃ | C₂H₅  | 100 |
| 92 | CH₃ | H | CH₃ |  | 100 |
| 95 | CH₃ | H | CH₃ |  | 100 |
| 41 | C₂H₅ | H | CH₃ |  | 100 |
| 44 | C₂H₅ | H | CH₃ |  | 100 |
| 53 | CH₃ | H | CH₃ |  | 100 |
| 56 | CH₃ | H | CH₃ |  | 100 |
| 37 | CH₃ | H | CH₃ | i-C₃H₇ | 100 |
| 38 | CH₃ | H | CH₃ | —CH₃ | 100 |
| 105 | CH₃ | CH₂Cl | H |  | 100 |
| 77 | C₂H₅ | CH₂Cl | H |  | 100 |

TABLE 6

Selective herbicidal action; postemergence treatment in the greenhouse

| Active ingredient no. | Formula | Appln. rate (kg a.i./ha) | Arachys hyp. | Glycine max | Sorgh. bicol. | Cassia spp. | Desmodium tort. | Nicand phys. | Sesban. exalt. |
|---|---|---|---|---|---|---|---|---|---|
| 34 | 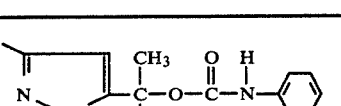 | 1.0 | 0 | 10 | 10 | 90 | 100 | 100 | 100 |
| | (U.S. Pat. No. 3,116,995) | 1.0 | 10 | 20 | 15 | 0 | 100 | 20 | 60 |
| | (German Laid-Open Application DE-OS 2,633,790) | 1.0 | 10 | 30 | 25 | 0 | 30 | 0 | 10 |

TABLE 7

Selective action in carrots; postemergence treatment in the greenhouse

| Active ingredient no. | Formula | Appln. rate (kg a.i./ha) | Daucus carota | Chenopod. alb. | Desmod. tort. | Sinapis alba |
|---|---|---|---|---|---|---|
| 36 | 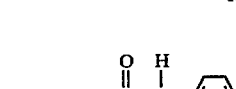 | 1.0 | 0 | 99 | 95 | 90 |
| | (U.S. Pat. No. 2,695,225) | 1.0 | 10 | 20 | 10 | 80 |

TABLE 8

Selective herbicidal action; postemergence treatment in the greenhouse

| Active ingredient no. | Formula | Appln. rate (kg a.i./ha) | Arachys hyp. | Tritic. aest. | Cent. cyan. | Matric. spp. | Nicand. phys. | Sinapis alba | Solan. nigr. |
|---|---|---|---|---|---|---|---|---|---|
| 35 | 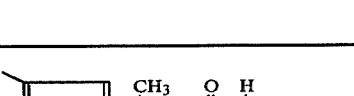 | 1.0 | 0 | 0 | 80 | 100 | 100 | 98 | 100 |
| | 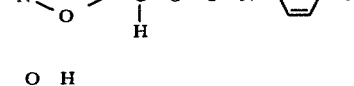 (U.S. Pat. No. 2,695,225) | 1.0 | 10 | 80 | — | 0 | 0 | 80 | 50 |

TABLE 8-continued

Selective herbicidal action; postemergence treatment in the greenhouse

| Active ingredient no. | Formula | Appln. rate (kg a.i./ha) | Arachys hyp. | Tritic. aest. | Cent. cyan. | Matric. spp. | Nicand. phys. | Sinapis alba | Solan. nigr. |
|---|---|---|---|---|---|---|---|---|---|
| | 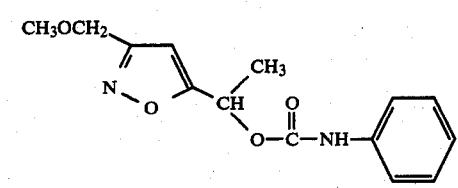 | 1.0 | 10 | 70 | — | 0 | 0 | 20 | 70 |

(German Laid-Open Application DE-OS 2,633,790)

TABLE 9

Selective control of unwanted grasses and broadleaved weeds; postemergence treatment in the greenhouse

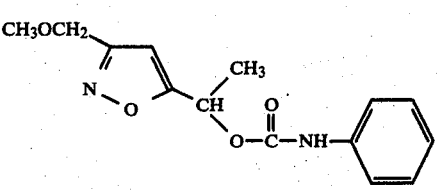

(No. 33)

| Test plants | % damage at 2.0 kg a.i/ha |
|---|---|
| Allium cepa | 0 |
| Beta vulgaris | 0 |
| Alopecurus myosuroides | 90 |
| Avena fatua | 80 |
| Bromus spp. | 90 |
| Centaurea cyanus | 80 |
| Datura stramonium | 80 |
| Sinapis alba | 100 |
| Stellaria media | 90 |

TABLE 10

Selective control of grassy weeds in rape; postemergence treatment in the greenhouse

| Active ingredient no. | | Appln. rate (kg a.i./ha) | Brassica napus | Alopec. myos. | Avena fatua |
|---|---|---|---|---|---|
| 98 | H₃C-[isoxazole]-CH(CH₃)-O-C(O)-NH-[m-CH₃-phenyl] | 1.0 | 0 | 100 | 90 |
| | 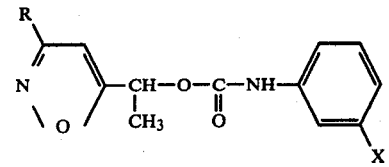 | 1.0 | 80 | 90 | 80 |

(U.S. Pat. No. 2,695,225)

TABLE 11

Selective control of *Chenopodium album* in sugarbeets and other crops; postemergence treatment in the greenhouse $$\underset{N\diagdown O}{R-}[\text{isoxazole}]-CH(CH_3)-O-C(O)-NH-[\text{phenyl-}X]$$

| Active ingredient no. | X | R | kg/ha a.i. | Arachys hyp. | Beta vulg. | Oryza sat. | Chenop. album |
|---|---|---|---|---|---|---|---|
| 13 | CH₃ | —CH₂—O—CH₃ | 1.0 | 0 | 0 | 10 | 100 |

TABLE 11-continued

Selective control of *Chenopodium album* in sugarbeets and other crops; postemergence treatment in the greenhouse

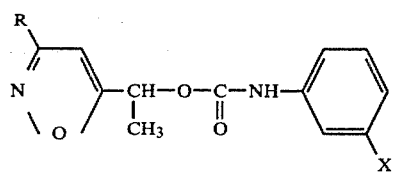

| Active ingredient no. | X | R | kg/ha a.i. | Arachys hyp. | Beta vulg. | Oryza sat. | Chenop. album |
|---|---|---|---|---|---|---|---|
| 21 | CF₃ | —COOC₂H₅ | 2.0 | 0 | 0 | 10 | 100 |
|  |  |  | 0.5 | 0 | 0 | 0 | 100 |
|  |  |  | 1.0 | 0 | 10 | 0 | 100 |

0 = no damage
100 = plants destroyed

TABLE 12

Selective weed control; postemergence application in the greenhouse

| Active ingredient no. | Structure | kg/ha a.i. | Test plants and % damage ||||||| 
|---|---|---|---|---|---|---|---|---|---|
|  |  |  | Arachys hyp. | Glycine max | Sorghum bicolor | Chenop. album | Datura stram. | Desmod. tort. | Mercur. ann. |
| 12 | CH₃—O—CH₂\N\O/CH—O—C—NH—⟨Cl⟩ | 0.5 | 0 | 0 | 0 | 100 | 100 | 100 | 90 |

0 = no damage
100 = plants destroyed

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* |  |
| *Brassica napus* var. *rapa* | turnips |
| *Brassica rapa* var. *silvestris* |  |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |

-continued

| Botanical name | Common name |
|---|---|
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* |  |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* |  |
| *Phaseolus lunatus* | limabeans |
| *Phaseolus mungo* | mungbeans |
| *Phaseolus vulgaris* | snapbeans, green beans, dry beans |
| *Pennisetum glaucum* |  |
| *Petroselinum crispum* | parsley |
| spp. *tuberosum* |  |
| *Picea abies* | Norway spruce |
| *Abies alba* | fir trees |
| *Pinus* spp. | pine trees |
| *Pisum sativum* | English peas |

| Botanical name | Common name |
| --- | --- |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

The new 1,2-oxazolyl alkyl carbamates according to the invention may, in addition to admixture among themselves, be mixed and applied together with numerous representatives of other herbicidal or growth-regulating active ingredient groups. Examples of suitable mixture components are diazines, N-phenylcarbamates, thiolcarbamates, halocarboxylic acids, phenoxy fatty acids, triazines, amides, ureas, diphenyl ethers, triazinones, uracils, benzofuran derivatives, etc. Such combinations broaden the spectrum of action and synergistic effects are sometimes achieved. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone 5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone 4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate 2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl, N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate 2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine 2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine 2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione 3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil 2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide 2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide 2-(2-methyl-4-chlorophenoxy-N-methoxyacetamide
2-(α-naphthoxy)-N,N-diethylpropionamide 2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-napthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylamino-phenylacetamide
N-4-methyl-5-(trifluoromethyl)-sulfonylamino-phenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile 3,5-dibromo-4-hydroxybenzonitrile (salts) 3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether 2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitro-phenyl ether
2-chloro-4-trifluoromethylphenyl-3'-carboxy-4'-nitro-phenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea 1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea 1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)

methyl α-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
sodium chlorate
ammonium thiocyanate
calcium cyanamide.

It may also be useful to apply the compounds according to the invention in admixture with other crop protection agents, e.g., agents for combating pests or phytopathogenic fungi or bacteria. The compounds may also be mixed with solutions of mineral matters used to remedy nutritional or trace element deficiencies. Oils of various types, oil concentrates, wetting agents, spreader-stickers and antifoams may be added to the individual active ingredients or mixtures thereof.

We claim:

1. A 1,2-oxazolyl alkyl carbamate of the formula

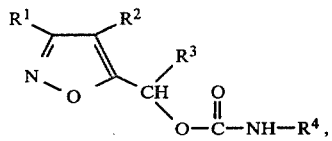

where $R^1$ is alkoxyalkyl of a maximum of 3 carbon atoms, or alkoxycarbonyl of a maximum of 5 carbon atoms, $R^2$ denotes hydrogen, or unsubstituted or halogen-substituted alkyl of a maximum of 3 carbon atoms, $R^3$ denotes hydrogen, or alkyl of a maximum of 3 carbon atoms, and $R^4$ denotes phenyl which is mono- or polysubstituted by halogen, nitro, cyano, linear or branched alkyl, alkoxy, haloalkyl, haloalkoxy, alkanoyl or alkoxycarbonyl, each of a maximum of 5 carbon atoms, or by cycloalkyl of from 3 to 6 carbon atoms.

2. A process for combating the growth of unwanted plants, wherein a herbicide is used which consists essentially of a 1,2-oxazolyl alkyl carbamate of the formula I as defined in claim 1.

3. 1-(3-Methoxymethyl-1,2-oxazol-5-yl)-ethyl-N-(3-chlorophenyl)-carbamate.

4. 1-(3-Methoxymethyl-1,2-oxazol-5-yl)-ethyl-N-(3-methylphenyl)-carbamate.

5. 1-(3-Methoxymethyl-1,2-oxazol-5-yl)-ethyl-N-(3-trifluoromethylphenyl)-carbamate.

6. A compound of the formula I as defined in claim 1 wherein $R^1$ is methoxymethyl.

7. A herbicide consisting essentially of a carrier and a herbicidally effective amount of at least one 1,2-oxazolyl alkyl carbamate of the formula I as defined in claim 1.

* * * * *